(12) United States Patent
Wass

(10) Patent No.: US 7,141,633 B2
(45) Date of Patent: Nov. 28, 2006

(54) OLEFIN TRIMERIZATION USING A CATALYST COMPRISING A SOURCE OF CHROMIUM, MOLYBDENUM OR TUNGSTEN AND A LIGAND CONTAINING AT LEAST ONE PHOSPHOROUS, ARSENIC OR ANTIMONY ATOM BOUND TO AT LEAST ONE (HETERO) HYDROCARBYL GROUP

(75) Inventor: Duncan Frank Wass, Twickenham (GB)

(73) Assignee: BP Chemicals Limited, London (GB)

( * ) Notice: Subject to any disclaimer, the term of this patent is extended or adjusted under 35 U.S.C. 154(b) by 0 days.

(21) Appl. No.: 10/920,262

(22) Filed: Aug. 18, 2004

(65) Prior Publication Data

US 2005/0020788 A1    Jan. 27, 2005

Related U.S. Application Data

(62) Division of application No. 10/332,584, filed as application No. PCT/GB01/03006 on Jul. 4, 2001, now Pat. No. 6,800,702.

(30) Foreign Application Priority Data

Jul. 11, 2000    (GB) ................................. 0016895.5

(51) Int. Cl.
  *C08F 4/69* (2006.01)
  *B01J 31/34* (2006.01)

(52) U.S. Cl. .................. 526/124.3; 526/129; 526/130; 526/133; 526/134; 526/161; 526/172; 502/104; 502/155; 502/167; 502/204

(58) Field of Classification Search ............. 526/124.3, 526/129, 130, 133, 134, 161, 172; 502/104, 502/155, 167, 204
See application file for complete search history.

(56) References Cited

U.S. PATENT DOCUMENTS

| 4,472,525 | A |   | 9/1984  | Singleton        |         |
|-----------|---|---|---------|------------------|---------|
| 4,668,838 | A | * | 5/1987  | Briggs           | 585/513 |
| 4,689,437 | A |   | 8/1987  | Murray           |         |
| 5,198,563 | A | * | 3/1993  | Reagen et al.    | 556/57  |
| 5,668,249 | A |   | 9/1997  | Baardman et al.  |         |
| 5,968,866 | A |   | 10/1999 | Wu               |         |

FOREIGN PATENT DOCUMENTS

| WO | WO97/37765   | 10/1997 |
| WO | WO01/10876 A1 | 2/2001 |

OTHER PUBLICATIONS

Hirsivaara et al., Journal of Organometallic Chemistry 579 (1999) 45-52.*

Hirsivaara et al., Journal of Organometallic Chemistry 579 (1999) 45-52.*

J. Pietsch et al., "Koordinationschemie funktioneller Phosphine II. Carbonyl(nitrosyl) wolfam-Komplexe mit 2-Diphenylphosphino-anisol sowie 2-Diphenylphosphinoanilid, -benzoat und—phenolat als Liganden", Journal of Organometallic Chemistry, vol. 495, pp. 113-125, (1995).

A. Ariffin et al., "The Asymmetric Synthesis of Phorphorus—and sulfur—containing tricarbonyl (.eta.6-arene) Chromium Complexes Using the Chiral Base Approach", J. Chem. Soc. Perkin Trans., vol. 21, pp. 3177-3189, (1999), Chemical Abstracts Service, Database Accession No. 132:108059.

L. Dahlenburg et al., "Koordinationschemie funktioneller Phosphane VIII. Tetracarbonylkomplexe des Wolframs und Molybdäns mit 2-(Diphenylophosphanyl)anilin-Liganden", Journal of Organometallic Chemistry, vol. 585, pp. 225-233, (1999).

Boni et al., "Heterobimetallic Dibridged Complexes [Cp2Ta(.mu.-CO)(.mu.—PMe2)M' (CO) 4] (M'=Cr, W): Synthesis and Reactivity Toward Two-Electron Donor Ligands L (L=PR3, Me2P(CH2) nPMe2, CNR)", Organometallics, vol. 14, No. 12, pp. 5652-5656, STN Database Accession No. 124:117494, (1995).

Dunbar et al., "Carbon Monoxide Reactions of the Fluxional Phosphine Complex (.eta. 3-PR3) Mo (CO)3 (R=2,4,6-Trimethoxyphenyl)", Organometallics, vol. 13, No. 7, pp. 2713-2720, STN Database Accession No. 121:72401, (1994).

Burgess et al., "Stereochemically matched (and mismatched) Bisphophine ligands: DIOP-DIPAMP Hybrids", Organometallics, vol. 11, No. 11, pp. 3588-3600, STN Database Assession No. 117:212586, (1992).

L. Hirsivaara et al., "Organometallic Derivatives of Multidentate Phosphines [o-(methylthio)phenyl]diphenylphosphine and bis(o-(methylthio)phenyl(phenylphosphine): preparation and characterization of Group 6 Metal Carbonyl Derivatives", Journal of Organometallic Chemistry, vol. 579, pp. 45-52, (1999).

L. Hirsivaara et al., "M(CO)6 (M=Cr, Mo, W) Derivatives of (o-anisyl) diphenylphosphine, bis(o-anisyl) phenylphosphine tris (o-anisyl) phosphine and (p-anisyl) bis (o-anisyl) phosphine", Inorg. Chim. ACTA, vol. 307 (1-2), pp. 47-56, STN Database Accession No. 134:36335, (2000).

* cited by examiner

*Primary Examiner*—Robert D. Harlan
(74) *Attorney, Agent, or Firm*—Finnegan, Henderson, Farabow, Garrett and Dunner, L.L.P.

(57) ABSTRACT

A process for the trimerization of olefins is disclosed, comprising contacting a monomeric olefin or mixture of olefins under trimerization conditions with a catalyst which comprises (a) a source of chromium, molybdenum or tungsten (b) a ligand containing at least one phosphorus, arsenic or antimony atom bound to at least one hydrocarbyl or heterohydrocarbyl group having a polar substituent, but excluding the case where all such polar substituents are phosphane, arsane or stibana groups; and optionally (c) an activator.

21 Claims, No Drawings

OLEFIN TRIMERIZATION USING A CATALYST COMPRISING A SOURCE OF CHROMIUM, MOLYBDENUM OR TUNGSTEN AND A LIGAND CONTAINING AT LEAST ONE PHOSPHOROUS, ARSENIC OR ANTIMONY ATOM BOUND TO AT LEAST ONE (HETERO) HYDROCARBYL GROUP

CROSS REFERENCE TO RELATED APPLICATIONS

This is a divisional of application Ser. No. 10/332,584, filed Jan. 10, 2003, now U.S. Pat. No. 6,800,702 which is a §371 of PCT/GB01/03006, filed Jul. 4, 2001, the contents of both of which are incorporated herein by reference.

This invention relates to the trimerisation of olefins, such as the preparation of 1-hexene by the trimerisation of ethylene.

U.S. Pat. No. 5,198,563 and related patents by Phillips describe chromium-containing catalysts containing monodentate amide ligands useful for trimerising olefins.

U.S. Pat. No. 5,968,866 discloses an ethylene oligomerisation/trimerisation process which uses a catalyst comprising a chromium complex which contains a coordinating asymmetric tridentate phosphane, arsane or stibane ligand (referred to therein as phosphine, arsine or stibine, and representing a phosphorus, arsenic or antimony atom attached to three hydrocarbyl groups) and an aluminoxane to produce alpha-olefins which are enriched in 1-hexene. There is no suggestion that it is possible to replace any of the phosphane, arsane or stibane groups: indeed, it is impossible to predict what the effect of such a replacement would be.

We have now discovered further ligands which when used in conjunction with a source of a Group 3 to 10 transition metal are significantly more active as trimerisation catalysts than those currently known, and also show other advantageous properties. The invention also encompasses within its scope novel catalysts comprising such ligands in conjunction with a source of chromium, molybdenum or tungsten.

Accordingly in a first aspect, the present invention provides a catalyst for the trimerisation of olefins, comprising (a) a source of chromium, molybdenum or tungsten;
(b) a ligand containing at least one phosphorus, arsenic or antimony atom bound to at least one hydrocarbyl or heterohydrocarbyl group having a polar substituent, but excluding the case where all such polar substituents are phosphane, arsane or stibane groups; and optionally
(c) an activator.

In this specification the term "trimerisation" means catalytic reaction of a single olefinic monomer or a mixture of olefinic monomers to give products enriched in those constituents derived from the reaction(s) of three olefinic monomers, as distinct from polymerisation or oligomerisation, which typically give olefinic product distributions governed by either a geometric series equation or following a Poisson pattern of distribution. "Trimerisation" includes the case where all the monomer units in the trimerisation product are identical, where the trimerization product is made from two different olefins (i.e. two equivalents of one monomer react with one equivalent of a second monomer), and also where three different monomer units react to yield the product. A reaction involving more than one monomer is often referred to as cotrimerisation.

It will be appreciated that the above catalyst may either be formed prior to use in a trimerisation reaction, or it may be formed in situ by adding the individual components thereof to the reaction mixture.

In a further aspect, the invention provides a process for the trimerisation of olefins, comprising contacting a monomeric olefin or mixture of olefins under trimerisation conditions with a catalyst which comprises (a) a source of a Group 3 to 10 transition metal;
(b) a ligand containing at least one phosphorus, arsenic or antimony atom bound to at least one hydrocarbyl or heterohydrocarbyl group having a polar substituent, but excluding the case where all such polar substituents are phosphane, arsane or stibane groups; and optionally
(c) an activator.

We have also found that the catalysts used in the above process have certain novel features. For example, such catalysts when supported lose less of their activity compared with the equivalent unsupported catalyst than known catalysts. A further aspect of the invention therefore is a supported catalyst having a productivity per mole of catalyst of at least 50%, preferably at least 70% of its productivity when unsupported, which catalyst preferably comprises (a) a source of a Group 3 to 10 transition metal;
(b) a ligand containing at least one phosphorus, arsenic or antimony atom bound to at least one hydrocarbyl or heterohydrocarbyl group having a polar substituent, but excluding the case where all such polar substituents are phosphane, arsane or stibane groups; and optionally
(c) an activator.

Additionally, we have found that such catalysts have unusually high productivity, and maintain that productivity particularly well. Accordingly one further aspect of the invention comprises a catalyst for the trimerisation of olefins, which has a productivity of at least 30000 g product per mmol catalyst per hour at a temperature of 110° C. or less and an ethylene partial pressure of 21 bar or less. Another aspect of the invention is a catalyst for the trimerisation of olefins, wherein the catalyst productivity decays at a rate of less than 10% per hour.

In one embodiment of the process of the invention, the catalyst utilised in the present invention additionally comprises a further catalyst (d) suitable for the polymerisation, oligomerisation or other chemical transformations of olefins. In processes wherein such an additional catalyst is present, the trimerisation products are incorporated into a higher polymer or other chemical product.

The catalysts used in the trimerisation process of the invention show exceptionally high productivity and selectivity to 1-hexene within the product fraction containing 6 carbon atoms. The high productivity of the catalysts results in greater process efficiency and/or lower intrinsic levels of catalyst residues. The high selectivity of the catalysts results in a greater ease of product purification (resulting either in less costly product purification or purer products). These advantages would be expected to apply both to processes wherein catalysts according to the invention comprise the sole catalytic component and also to integrated processes, for example in the production of branched polyolefins, where more than one transition metal catalyst is employed.

As regards the source of Group 3 to 10 transition metal (a), this can include simple inorganic and organic salts, for example, halides, acetylacetonates, carboxylates, oxides, nitrates, sulfates and the like, as well as co-ordination and organometallic complexes, for example, chromium trichloride tetrahydrofuran complex, (benzene)tricarbonylchromium, chromium hexacarbonyl, molybdenum hexacarbonyl and the like. Preferably component (a) is a source of chromium, molybdenum or tungsten; particularly preferred is chromium.

The ligand of component (b) preferably has the formula

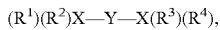

wherein

X is phosphorus, arsenic or antimony;

Y is a linking group;

and $R^1$, $R^2$, $R^3$ and $R^4$ are each independently hydrocarbyl, substituted hydrocarbyl, heterohydrocarbyl or substituted heterohydrocarbyl groups, at least one of which has a polar substituent which is not a phosphane, arsane or stibane group.

An alternative preferred structure for the ligand of component (b) is $X(R^1)(R^2)(R^3)$ wherein X and $R^1$, $R^2$ and $R^3$ are as defined above, with at least one of $R^1$, $R^2$ and $R^3$ having a polar substituent which is not a phosphane, arsane or stibane group.

X is preferably phosphorus. As regards $R^1$, $R^2$, $R^3$ and $R^4$, examples of suitable hydrocarbyl groups are methyl, ethyl, ethylenyl, propyl, butyl, cyclohexyl, benzyl, phenyl, tolyl, xylyl, mesityl, biphenyl, naphthyl, anthracenyl and the like. Examples of suitable heterohydrocarbyl groups are methoxy, ethoxy, phenoxy (i.e. $-OC_6H_5$), tolyloxy (i.e. $-OC_6H_4(CH_3)$), xylyloxy, mesityloxy, dimethylamino, diethylamino, methylethylamino, thiomethyl, thiophenyl, trimethylsilyl, dimethylhydrazyl and the like.

Preferably those of $R^1$ to $R^4$ having polar substituents are substituted aryl groups with at least one polar substituent. Suitable substituted aryl groups include substituted phenyl, substituted naphthyl and substituted anthracenyl groups. Substituted phenyl is preferred. Polar substituents include methoxy, ethoxy, isopropoxy, $C_3$–$C_{20}$ alkoxy, phenoxy, pentafluorophenoxy, trimethylsiloxy, dimethylamino, methylsulphanyl, tosyl, methoxymethyl, methylthiomethyl, 1,3-oxazolyl, methoxymethoxy, hydroxyl, amino, sulphate, nitro and the like. Other suitable polar substituents include phosphanes, arsanes and stibanes as described in U.S. Pat. No. 5,968,866 (but subject to the above-mentioned proviso that at least one of $R^1$ to $R^4$ has a polar substituent which is not one of these). Ortho-substituted phenyl groups are most preferred; the ortho substituent is preferably alkoxy, more preferably methoxy or methoxymethoxy. The phenyl groups may additionally be substituted in the meta and para or other ortho positions by groups such as hydrocarbyl, heterohydrocarbyl, substituted hydrocarbyl, halide and the like; but it is preferred that they are unsubstituted in these other positions.

Preferably any of $R^1$ to $R^4$ which do not have polar substituents are independently optionally substituted phenyl groups; substituents may be hydrocarbyl, heterohydrocarbyl, substituted hydrocarbyl, substituted heterohydrocarbyl, halide and the like. However it is most preferred that all of $R^1$ to $R^4$ have polar substituents as defined above, which are not phosphane, arsane or stibane groups. It is also most preferred that $R^1$ to $R^4$ are the same.

Y may be any bridging group, for example hydrocarbyl, substituted hydrocarbyl, heterohydrocarbyl, substituted hydrocarbyl or substituted heterohydrocarbyl bridging groups, or inorganic bridging groups including single atom links such as —O—. Y may optionally contain an additional potential donor site. Examples of Y include methylene, 1,2-ethane, 1,2-phenylene, 1,3-propane, 1,2-catechol, 1,2-dimethylhydrazine, $-N(R^5)-$ where $R^5$ is hydrogen, hydrocarbyl, or substituted hydrocarbyl, and the like. Preferably Y is $-N(R^5)-$; preferably $R^5$ is hydrogen, $C_1$–$C_6$ alkyl or phenyl, more preferably methyl.

Any of the groups $R^1$–$R^4$ may independently be linked to one or more of each other or to the bridging group Y, to form a cyclic structure together with X or X and Y.

The ligands can be prepared using procedures known to one skilled in the art and disclosed in published literature. Examples of preferred compounds are:

(2-methoxyphenyl)(phenyl)PN(Me)P(phenyl)$_2$
(2-methoxyphenyl)$_2$PN(Me)P(phenyl)$_2$
(2-methoxyphenyl)(phenyl)PN(Me)P(2-methoxyphenyl)(phenyl)
(2-methoxyphenyl)$_2$PN(Me)P(2-methoxyphenyl)$_2$
(2-ethoxyphenyl)$_2$PN(Me)P(2-ethoxyphenyl)$_2$
(2-isopropoxyphenyl)$_2$PN(Me)P(2-isopropoxyphenyl)$_2$
(2-hydroxyphenyl)$_2$PN(Me)P(2-hydroxyphenyl)$_2$
(2-nitrophenyl)$_2$PN(Me)P(2-nitrophenyl)$_2$
(2,3-dimethoxyphenyl)$_2$PN(Me)P(2,3dimethoxyphenyl)$_2$
(2,4-dimethoxyphenyl)$_2$PN(Me)P(2,4-dimethoxyphenyl)$_2$
(2,6-dimethoxyphenyl)$_2$PN(Me)P(2,6-dimethoxyphenyl)$_2$
(2,4,6-trimethoxyphenyl)$_2$PN(Me)P(2,4,6-trimethoxyphenyl)$_2$
(2-dimethoxyphenyl)(2-methylphenyl)PN(Me)P(2-methylphenyl)$_2$
[2-(dimethylamino)phenyl]$_2$PN(Me)P[2-(dimethylamino)phenyl]$_2$
(2-methoxymethoxyphenyl)$_2$PN(Me)P(2-methoxymethoxyphenyl)$_2$
(2-methoxyphenyl)$_2$PN(Ethyl)P(2-methoxyphenyl)$_2$
(2-methoxyphenyl)$_2$PN(Phenyl)P(2-methoxyphenyl)$_2$
(2-methoxyphenyl)$_2$PN(Me)N(Me)P(2-methoxyphenyl)$_2$
(2-methoxyphenyl)$_2$PCH$_2$P(2-methoxyphenyl)$_2$
(2-methoxyphenyl)$_2$PCH$_2$CH$_2$P(2-methoxyphenyl)$_2$
tri(2-methoxymethoxyphenyl)phosphane i.e.

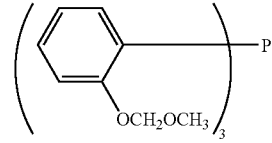

tri(2-methoxyphenyl)phosphane.

Components (a) and (b) may be present in any ratio, preferably between 10000:1 and 1:10000; more preferred is a ratio between 100:1 and 1:100, and especially preferred is a ratio of 10:1 to 1:10, particularly 3:1 to 1:3. Generally the amounts of (a) and (b) are approximately equal, ie a ratio of between 1.5:1 and 1:1.5.

The activator compound (c) may in principle of be any compound that generates an active catalyst with components a) and b). Mixtures of activators may also be used. Suitable compounds include organoaluminium compounds, organoboron compounds and inorganic acids and salts, such as tetrafluoroboric acid etherate, silver tetrafluoroborate, sodium hexafluoroantimonate and the like. Suitable organoaluminium compounds include compounds of the formula AlR$_3$, where each R is independently $C_1$–$C_{12}$ alkyl, oxygen or halide, and compounds such as LiAlH$_4$ and the like. Examples include trimethylaluminium (TMA), triethylaluminium (TEA), tri-isobutylaluminium (TIBA), tri-n-octylaluminium, methylaluminium dichloride, ethylaluminium dichloride, dimethylaluminium chloride, diethylaluminium chloride, ethylaluminiumsesquichloride, methylaluminiumsesquichloride, and alumoxanes. Alumoxanes are well known in the art as typically oligomeric compounds which can be prepared by the controlled addition of water to an alkylaluminium compound, for example trimethylaluminium. Such compounds can be linear, cyclic, cages or mixtures thereof. Commercially available alumoxanes are generally believed to be mixtures of linear and cyclic compounds. The cyclic alumoxanes can be represented by the formula $[R^6AlO]_s$ and the linear alumoxanes by the formula $R^7(R^8AlO)_s$ wherein s is a number from about 2 to 50, and wherein $R^6$, $R^7$, and $R^8$ represent hydrocarbyl groups, preferably $C_1$ to $C_6$ alkyl groups, for example methyl, ethyl or butyl groups. Alkylalumoxanes such as methylalumoxane (MAO) are preferred.

Mixtures of alkylalumoxanes and trialkylaluminium compounds are particularly preferred, such as MAO with TMA or TIBA. In this context it should be noted that the term "alkylalumoxane" as used in this specification includes alkylalumoxanes available commercially which may contain a proportion, typically about 10 wt %, but optionally up to 50 wt %, of the corresponding trialkylaluminium; for instance, commercial MAO usually contains approximately 10 wt % trimethylaluminium (TMA), whilst commercial MMAO contains both TMA and TIBA. Quantities of alkylalumoxane quoted herein include such trialkylaluminium impurities, and accordingly quantities of trialkylaluminium compounds quoted herein are considered to comprise compounds of the formula $AlR_3$ additional to any $AlR_3$ compound incorporated within the alkylalumoxane when present.

Examples of suitable organoboron compounds are boroxines, $NaBH_4$, trimethylboron, triethylboron, dimethylphenylammoniumtetra(phenyl)borate, trityltetra(phenyl)borate, triphenylboron, dimethylphenylammonium tetra(pentafluorophenyl)borate, sodium tetrakis[(bis-3,5-trifluoromethyl)phenyl]borate, $H^+(OEt_2)_2$[(bis-3,5-trifluoromethyl)phenyl]borate, trityltetra(pentafluorophenyl)borate and tris(pentafluorophenyl) boron.

Activator compound (c) may also be or contain a compound that acts as a reducing or oxidising agent, such as sodium or zinc metal and the like, or oxygen and the like.

In the preparation of the catalysts utilised in the present invention, the quantity of activating compound to be employed is easily determined by simple testing, for example, by the preparation of small test samples which can be used to trimerise small quantities of the monomer(s) and thus to determine the activity of the produced catalyst It is generally found that the quantity employed is sufficient to provide 0.1 to 20,000 atoms, preferably 1 to 2000 atoms of aluminium or boron per atom of chromium. In some cases, for particular combinations of component a) and b), an activating compound c) may not be required.

Components (a)–(c) of the catalyst system utilised in the present invention may be added together simultaneously or sequentially, in any order, and in the presence or absence of monomer in any suitable solvent, so as to give an active catalyst. For example, components (a), (b) and (c) and monomer may be contacted together simultaneously, or components (a), (b) and (c) may be added together simultaneously or sequentially in any order and then contacted with monomer, or components a) and b) may be added together to form an isolable metal-ligand complex and then added to component c) and contacted with monomer, or components (a), (b) and (c) may be added together to form an isolable metal-ligand complex and then contacted with monomer. Suitable solvents for contacting the components of the catalyst or catalyst system include, but are not limited to, hydrocarbon solvents such as heptane, toluene, 1-hexene and the like, and polar solvents such as diethyl ether, tetrahydrofuran, acetonitrile, dichloromethane, chloroform, chlorobenzene, methanol, acetone and the like.

The catalyst components (a), (b) and (c) utilised in the present invention can be unsupported or supported on a support material, for example, silica, alumina, $MgCl_2$ or zirconia, or on a polymer, for example polyethylene, polypropylene, polystyrene, or poly(aminostyrene). It is an advantage of the present invention that very little productivity (mass of product per mol of catalyst per hour) is lost when the catalyst is supported. If desired the catalysts can be formed in situ in the presence of the support material, or the support material can be pre-impregnated or premixed, simultaneously or sequentially, with one or more of the catalyst components. The quantity of support material employed can vary widely, for example from 100,000 to 1 grams per gram of metal present in the transition metal compound. In some cases, the support may material can also act as or as a component of the activator compound (c). Examples include supports containing alumoxane moieties and/or hydrocarbyl boryl moieties (see, for example, Hlatky, G. G. Chem. Rev. 2000, 100, 1347.)

One embodiment of the present invention encompasses the use of components (a) (b) and optionally (c) in conjunction with one or more types of olefin polymerisation catalyst or catalyst system (d) to trimerise olefins and subsequently incorporate a portion of the trimerisation product(s) into a higher polymer.

Component (d) may be one or more suitable polymerisation catalyst(s) or catalyst system(s), examples of which include, but are not limited to, conventional Ziegler-Natta catalysts, metallocene catalysts, monocyclopentadienyl or "constrained geometry" catalysts, heat activated supported chromium oxide catalysts (eg. "Phillips"-type catalysts), late transition metal polymerisation catalysts (eg. diimine, diphosphine and salicylaldimine nickel/palladium catalysts, iron and cobalt pyridyldiimine catalysts and the like) and other so-called "single site catalysts" (SSC's).

Ziegler-Natta catalysts, in general, consist of two main components. One component is an alkyl or hydride of a Group I to III metal, most commonly $Al(Et)_3$ or $Al(iBu)_3$ or $Al(Et)_2Cl$ but also encompassing Grignard reagents, n-butyllithium, or dialkylzinc compounds. The second component is a salt of a Group IV to VIII transition metal, most commonly halides of titanium or vanadium such as $TiCl_4$, $TiCl_3$, $VCl_4$, or $VOCl_3$. The catalyst components when mixed, usually in a hydrocarbon solvent, may form a homogeneous or heterogeneous product. Such catalysts may be impregnated on a support, if desired, by means known to those skilled in the art and so used in any of the major processes known for co-ordination catalysis of polyolefins such as solution, slurry, and gas-phase. In addition to the two major components described above, amounts of other compounds (typically electron donors) maybe added to further modify the polymerization behaviour or activity of the catalyst.

Metallocene catalysts, in general, consist of transistion metal complexes, most commonly based on Group IV metals, ligated with cyclopentadienyl(Cp)-type groups. A wide range of structures of this type of catalysts is known, including those with substituted, linked and/or heteroatom-containing Cp groups, Cp groups fused to other ring systems and the like. Additional activators, such as boranes or alumoxane, are often used and the catalysts may be supported, if desired.

Monocyclopentadienyl or "constrained geometry" catalysts, in general, consist of a transition metal complexes, most commonly based on Group IV metals, ligated with one cyclopentadienyl(Cp)-type group, often linked to additional donor group. A wide range of structures of this type of catalyst is known, including those with substituted, linked and/or heteroatom-containing Cp groups, Cp groups fused to other ring systems and a range of linked and non-linked additional donor groups such as amides, amines and alkoxides. Additional activators, such as boranes or alumoxane, are often used and the catalysts may be supported, if desired.

A typical heat activated chromium oxide (Phillips) type catalyst employs a combination of a support material to which has first been added a chromium-containing material wherein at least part of the chromium is in the hexavalent state by heating in the presence of molecular oxygen. The support is generally composed of about 80 to 100 wt. % silica, the remainder, if any, being selected from the group consisting of refractory metal oxides, such as aluminium, boria, magnesia, thoria, zirconia, titania and mixtures of two or more of these refractory metal oxides. Supports can also comprise alumina, aluminium phosphate, boron phosphate and mixtures thereof with each other or with silica. The chromium compound is typically added to the support as a chromium (III) compound such as the acetate or acetylacetonate in order to avoid the toxicity of chromium (VI). The raw catalyst is then calcined in air at a temperature between 250 and 1000° C. for a period of from a few seconds to several hours. This converts at least part of the chromium to the hexavalent state. Reduction of the Cr (VI) to its active form normally occurs in the polymerization reaction, but can be done at the end of the calcination cycle with CO at about 350° C. Additional compounds, such as fluorine, aluminium and/or titanium may be added to the raw Phillips catalyst to modify it.

Late transition metal and single site catalysts cover a wide range of catalyst structures based on metals across the transition series (see, for example, Britovsek, G. J. P et al. *Angew. Chem. Int. Ed. Engl.* 1999, 38, 429. and Ittel, S. D. et al. *Chem. Rev.* 2000, 100, 1169.

Component (d) may also comprise one or more polymerisation catalysts or catalyst systems together with one or more additional oligomerisation catalysts or catalyst systems. Suitable oligomerisation catalysts include, but are not limited to, those that dimerise (for example, nickel phosphine dimerisation catalysts) or trimerise olefins or otherwise oligomerise olefins to, for example, a distribution of 1-olefins governed by a geometric series equation (for example, iron and cobalt pyridyldiimine oligomerisation catalysts).

Component (d) may independently be supported or unsupported. Where components (a) and (b) and optionally (c) are supported, (d) may be co-supported sequentially in any order or simultaneously on the same support or may be on a separate support. For some combinations, the components (a)–(c) may be part or all of component (d). For example, if component (d) is a heat activated chromium oxide catalyst then this may be (a), a chromium source and if component (d) contains an alumoxane activator then this may also be the optional activator (c).

The components (a), (b), (c) and (d) may be in any molar ratio. In the context of an integrated process the ratio of (a) to (d) is seen as particularly important. The ratio of (a) to (d) is preferably from 10000:1 to 1:10000 and more preferably from 100:1 to 1:100. The precise ratio required depends on the relative reactivity of the components and also on the desired properties of the product or catalyst systems.

Suitable olefinic monomers, or combinations thereof for use in the trimerisation process of the present invention are hydrocarbon olefins, for example, ethylene, $C_{2-20}$ α-olefins, internal olefins, vinylidene olefins, cyclic olefins and dienes, propylene, 1-butene, 1-pentene, 1-hexene, 4-methylpentene-1, 1-heptene, 1-octene, 1-nonene, 1-decene, 1-undecene, 1-dodecene, 1-tridecene, 1-tetradecene, 1-pentadecene, 1-hexadecene, 1-heptadecene, 1-octadecene, 1-nonadecene, 1-eicosene, styrene, 2-butene, 2-ethyl-1-hexene, cyclohexene, norbornene, butadiene and 1,5-hexadiene. Olefins with a polar functionality, such as methyl (meth)acrylate, vinyl acetate, α,ω-undecenol and the like, may also be used. The preferred monomer is ethylene. Mixtures of these monomer may also be used, for example a 1-butene unit and two ethylene units may be co-trimerised to form C8 olefins, or 1-hexene and ethylene co-trimerised to C10 olefins, or 1-dodecene and ethylene co-trimerised to C16 olefins. Combinations of these co-trimerisation reactions may be performed simultaneously, especially when one or more of the monomers are produced in-situ (e.g. a mixture of ethylene and butene can be used to form mixtures containing predominantly hexenes, octenes, and decenes.) Techniques for varying the distribution of products from these reactions include controlling process conditions (e.g. concentration, reaction temperature, pressure, residence time) and properly selecting the design of the process and are well known to those skilled in the art. These monomers or combinations thereof are also suitable in the presence of component (d).

Olefinic monomers or mixtures of olefinic monomers for trimerisation may be substantially pure or may contain olefinic impurities. One embodiment of the process of the invention comprises the trimerisation of olefin-containing waste streams from other chemical processes or other stages of the same process.

When operating under solution or slurry phase conditions, any diluent or solvent that is an olefin, a mixture of olefins, or is substantially inert under trimerisation conditions may be employed. Mixtures of inert diluents, with or without one or more olefins, also could be employed. The preferred diluents or solvents are aliphatic and aromatic hydrocarbons and halogenated hydrocarbons such as, for example, isobutane, pentane, toluene, xylene, ethylbenzene, cumene, mesitylene, heptane, cyclohexane, methylcyclohexane, 1-hexene, 1-octene, chlorobenzene, dichlorobenzene, and the like, and mixtures such as isopar.

The trimerisation conditions can be, for example, solution phase, slurry phase, gas phase or bulk phase, with temperatures ranging from $-100°$ C. to $+300°$ C., preferably from 0° C. to +300° C. and more preferably from 35° C. to 200° C., and at pressures of atmospheric and above, preferably from atmospheric to 800 barg and more preferably from 1 barg to 100 barg. If desired, the process can be operated at temperatures above 120° C., and optionally also at pressures below 30 barg. The high initial rate and low rate of deactivation of this catalyst system enables lower pressures to be employed than would have been economically feasible with prior art catalyst systems.

Irrespective of the trimerisation technique employed, trimerisation is typically carried out under conditions that substantially exclude oxygen, water, and other materials that act as catalyst poisons. Also, trimerisation can be carried out in the presence of additives to control selectivity, enhance activity and reduce the amount of polymer formed in trimerisation processes. Suitable additives include, but are not limited to, hydrogen or a halide source such as $GeCl_4$. Exemplary halides include, but are not limited to fluoride, chloride, bromide, and/or iodide.

There exist a number of options for the trimerisation reactor including batch, semi-batch, and continuous operation. The trimerisation and co-trimerisation reactions of the present invention can be performed under a range of process conditions that are readily apparent to those skilled in the art: as a homogeneous liquid phase reaction in the presence or absence of an inert hydrocarbon diluent such as toluene or heptanes; as a two-phase liquid/liquid reaction; as a slurry process where the catalyst is in a form that displays little or no solubility; as a bulk process in which essentially neat reactant and/or product olefins serve as the dominant medium; as a gas-phase process in which at least a portion of the reactant or product olefin(s) are transported to or from a supported form of the catalyst via the gaseous state. Evaporative cooling from one or more monomers or inert volatile liquids is but one method that can be employed to effect the removal of heat from the reaction. The trimerisation reactions may be performed in the known types of gas-phase reactors, such as circulating bed, vertically or horizontally stirred-bed, fixed-bed, or fluidised-bed reactors, liquid-phase reactors, such as plug-flow, continuously stirred tank, or loop reactors, or combinations thereof. A wide range of methods for effecting product, reactant, and catalyst separation and/or purification are known to those skilled in the art and may be employed: distillation, filtration, liquid-liquid separation, slurry settling, extraction, etc. One or more of these methods may be performed separately from the trimerisation reaction or it may be advantageous to integrate at least some with a trimerisation reaction; a non-limiting example of this would be a process employing catalytic (or reactive) distillation. Also advantageous may be a process which includes more than one reactor, a catalyst kill system between reactors or after the final reactor, or an integrated reactor/separator/purifier. While all catalyst components, reactants, inerts, and products could be employed in the present invention on a once-through basis, it is often economically advantageous to recycle one or more of these materials; in the case of the catalyst system, this might require reconstituting one or more of the catalysts components to achieve the active catalyst system. It is within the scope of this invention that a trimerisation product might also serve as a reactant (e.g. 1-hexene, produced via the trimerization of ethylene, might be converted to decene products via a subsequent co-trimerization reaction with ethylene.)

A number of process options can be envisaged when using the catalysts of the present invention in an integrated process that includes a subsequent chemical transformation, i.e. with component (d) present. These options include "in series" processes in which the trimerisation and subsequent reaction are performed in separate, linked reactors, optionally with recycling of products/reagents between the reactors, and "in situ" processes in which a both reaction steps are carried out in the same reactor. Chemical transformations involving olefins are well known to those skilled in the art: non-limiting examples of the chemical reactions that might be effected by use of a component (d) include polymerisation and co-polymerisation, oligomerisation, hydrogenation, hydroformylation, oxidation, hydration, sulfonation, epoxidation, isomerisation, amination, cyclisation, and alkylation. A typical reactor residence time in the polymerisation reactor is less than 4 hours, preferably less than 3 hours.

In the case of an "in series" process various purification, analysis and control steps for the oligomeric product could potentially be incorporated between the trimerization and subsequent reaction stages. Recycling between reactors configured in series is also possible. An example of such a process would be the trimerisation of ethylene in a single reactor with a catalyst comprising components (a), (b) and optionally (c) followed by polymerisation of the trimerisation product with ethylene in a separate, linked reactor to give branched polyethylene. Another example would be co-trimerisation of ethylene and 1-butene and subsequent polymerisation of the trimerisation product to give poly (octene). Another example would be the trimerisation of an ethylene-containing waste stream from a polyethylene process, followed by introduction of the product 1-hexene back into the polyethylene process as a co-monomer for the production of branched polyethylene.

An example of an "in situ" process is the production of branched polyethylene catalysed by components (a), (b), (d) and optionally (c), added in any order such that the active catalytic species derived from components (a), (b) and optionally (c) is/are at some point present in a reactor with component (d)

Both the "in series and "in situ" approaches can be adaptions of current polymerisation technology for the process stages including component (d). All major olefin existing polymerisation processes, including multiple reactor processes, are considered adaptable to this approach. One adaption is the incorporation of a trimerisation catalyst bed into a recycle loop of a gas phase polymerisation process, this could be as a side or recycle stream within the main fluidisation recycle loop and or within the degassing recovery and recycle system.

Polymerisation conditions when component (d) is present can be, for example, solution phase, slurry phase, gas phase or bulk phase, with temperatures ranging from $-100°$ C. to $+300°$ C., and at pressures of atmospheric and above, particularly from 1.40 to 41 bar. Reaction conditions, will typically have a significant impact upon the properties (e.g. density, melt index, yield) of the polymer being made and it is likely that the polymer requirements will dictate many of the reaction variables. Reaction temperature, particularly in processes where it is important to operate below the sintering temperature of the polymer, will typically, and preferably, be primarily selected to optimise the polymerisation reaction conditions. The high productivity, and kinetic profile characteristics, of this new trimerisation catalyst makes the 'in-situ' production of the comonomer, preferably hexene-1, during polymer, preferably polyethylene, production far more commercially attractive than prior art catalysts systems. This is true even at the typical reaction temperatures and pressures for the production of polyethylenes with high comonomer contents such as LLDPE, VLDPE and ULDPE (preferably between 50° C. and 100° C., depending upon the density of the polymer) and even when used in slurry and gas phase polymerisation processes (preferably total gas phase pressures between 15 and 30 bar and ethylene pressures between 10 and 70 percent of the gas phase). If desired, the catalyst can be used to polymerise ethylene under high pressure/high temperature process conditions wherein the polymeric material forms as a melt in supercritical ethylene. Preferably the polymerisation is conducted under gas phase fluidized bed or stirred bed conditions. Also, polymerisation or copolymerisation can be carried out in the presence of additives to control polymer or copolymer molecular weights. The use of hydrogen gas as a means of controlling the average molecular weight of the polymer or copolymer applies generally to the polymerization process of the present invention.

Slurry phase polymerisation conditions or gas phase polymerisation conditions are particularly useful for the production of high or low density grades of polyethylene, and polypropylene. In these processes the polymerisation conditions can be batch, continuous or semi-continuous. Furthermore, one or more reactors may be used, e.g. from two to five reactors in series. Different reaction conditions, such as different temperatures or hydrogen concentrations may be employed in the different reactors. In cascade operation the trimerisation catalyst may be added to any or all of the polymerisation reactors concerned. If added to the first reactor and carried through to subsequent reactors, the trimerisation catalyst may, or may not, be supplemented in subsequent reactors with fresh trimerisation or polymerisation catalyst, it may be deactivated in subsequent reactors through addition of reversible or irreversible poisons that partially or fully kill the trimerisation catalyst or though addition of additional polymerisation catalysts or modifiers that deactivate the trimerisation catalyst.

In the slurry phase process and the gas phase process, the catalyst is generally supported and metered and transferred into the polymerization zone in the form of a particulate solid either as a dry powder (e.g. with an inert gas, ethylene or an olefin) or as a slurry. In addition, an optional activator can be fed to the polymerisation zone, for example as a solution, separately from or together with the solid catalyst. Components (a)–(d) can be added to any part of the polymerisation reactor either on the same support particle or as a physical mixture on different support particles, or may be added separately to the same or different parts of the reactor sequentially in any order or simultaneously. Alternatively, (a)–(d) may be unsupported and independently added to any part of the polymerisation reactor simultaneously or sequentially together or separately. The ratio of the primary monomer to the other (co)monomers has a significant impact on the properties of the polymer formed (eg density) and it is usually desirable to be tightly controlled. This ratio may be primarily controlled by altering the concentration or partial pressure of either the primary monomer and/or the comonomer(s). Typically the primary monomer concentration will be controlled independently of the ratio to comonomers (for other reasons such as activity) and the primary monomer to comonomer ratio(s) may be controlled by varying the rate of introduction of trimerisation catalyst or by altering reaction conditions which preferentially impact the trimerisation reaction over the polymerisation reaction or which impacts upon the distribution of comonomers actually formed (eg by using reversible poisons/activators). Fresh comonomer feed may additionally be introduced to the polymerisation reactor to control the ratio. It may be desirable to preferentially purge certain (co)monomer(s) that are formed in the trimerisation reaction by, for example, heating or cooling a vapour (or liquid) slip (or recycle) stream within the polymerisation reaction (or degassing) systems. This may for example be optimised by controlling compressor knock-out or interstage conditions in recycle or degassing vent recovery compressors or by using dedicated condensing exchangers or distillation apparatus.

The rate of addition of each component may be independently controlled to allow variations in the ratio of components and the density of the polymer produced. Pressure, temperature, hydrogen addition, halogenated hydrocarbon addition, electron donor addition, activator/retarder addition and other suitable variables may also be varied to control the activity of each component and also allow control of the polymer produced.

Once the polymer product is discharged from the reactor, any associated and absorbed hydrocarbons are substantially removed, or degassed, from the polymer by, for example, pressure let-down or gas purging using fresh or recycled steam, nitrogen or light hydrocarbons (such as ethylene). Recovered gaseous or liquid hydrocarbons may be recycled to a purification system or the polymerisation zone.

In the slurry phase polymerisation process the polymerisation diluent is compatible with the polymer(s) and catalysts, and may be an alkane such as hexane, heptane, isobutane, or a mixture of hydrocarbons or paraffins. The polymerization zone can be, for example, an autoclave or similar reaction vessel, or a continuous liquid full loop reactor, e.g. of the type well-known in the manufacture of polyethylene by the Phillips Process. When the polymerisation process of the present invention is carried out under slurry conditions the polymerisation is preferably carried out at a temperature above 0° C., most preferably above 15° C. Under slurry conditions the polymerisation temperature is preferably maintained below the temperature at which the polymer commences to soften or sinter in the presence of the polymerisation diluent. If the temperature is allowed to go above the latter temperature, fouling of the reactor can occur. Adjustment of the polymerisation within these defined temperature ranges can provide a useful means of controlling the average molecular weight of the produced polymer. A further useful means of controlling the molecular weight is to conduct the polymerization in the presence of hydrogen gas which acts as chain transfer agent. Generally, the higher the concentration of hydrogen employed, the lower the average molecular weight of the produced polymer.

In bulk polymerisation processes, liquid monomer such as propylene is used as the polymerisation medium.

Methods for operating gas phase polymerisation processes are well known in the art. Such methods generally involve agitating (e.g. by stirring, vibrating or fluidising) a bed of catalyst, or a bed of the target polymer (i.e. polymer having the same or similar physical properties to that which it is desired to make in the polymerisation process) containing a catalyst, and feeding thereto a stream of monomer (under conditions such that at least part of the monomer polymerises in contact with the catalyst in the bed. The bed is generally cooled by the addition of cool gas (e.g. recycled gaseous monomer) and/or volatile liquid (e.g. a volatile inert hydrocarbon, or gaseous monomer which has been condensed to form a liquid). The polymer produced in, and isolated from, gas phase processes forms directly a solid in the polymerisation zone and is free from, or substantially free from liquid. As is well known to those skilled in the art, if any liquid is allowed to enter the polymerisation zone of a gas phase polymerisation process the quantity of liquid in the polymerisation zone is small in relation to the quantity of polymer present. This is in contrast to "solution phase" processes wherein the polymer is formed dissolved in a solvent, and "slurry phase" processes wherein the polymer forms as a suspension in a liquid diluent.

The gas phase process can be operated under batch, semi-batch, or so-called "continuous" conditions. It is preferred to operate under conditions such that monomer is continuously recycled to an agitated polymerisation zone containing polymerisation catalyst, make-up monomer being provided to replace polymerised monomer, and continuously or intermittently withdrawing produced polymer from the polymerisation zone at a rate comparable to the rate of formation of the polymer, fresh catalyst being added to the polymerisation zone to replace the catalyst withdrawn from the polymerisation zone with the produced polymer.

Methods for operating gas phase fluidized bed processes for making polyethylene, ethylene copolymers and polypropylene are well known in the art. The process can be operated, for example, in a vertical cylindrical reactor equipped with a perforated distribution plate to support the bed and to distribute the incoming fluidising gas stream through the bed. The fluidising gas circulating through the bed serves to remove the heat of polymerisation from the bed and to supply monomer for polymerization in the bed. Thus the fluidising gas generally comprises the monomer(s) normally together with some inert gas (e.g. nitrogen or inert hydrocarbons such as methane, ethane, propane, butane, pentane or hexane) and optionally with hydrogen as molecular weight modifier. The hot fluidising gas emerging from the top of the bed is led optionally through a velocity reduction zone (this can be a cylindrical portion of the reactor having a wider diameter) and, if desired, a cyclone and or filters to disentrain fine solid particles from the gas stream. The hot gas is then led to a heat exchanger to remove at least part of the heat of polymerisation. Catalysts are preferably fed continuously or at regular intervals to the bed. At start up of the process, the bed comprises fluidisable polymer which is preferably similar to the target polymer. Polymer is produced continuously within the bed by the polymerization of the monomer(s). Preferably means are provided to discharge polymer from the bed continuously or at regular intervals to maintain the fluidized bed at the desired height. The process is generally operated at relatively low pressure, for example, at 10 to 50 bars, and at temperatures for example, between 50 and 135° C. The temperature of the bed is maintained below the sintering temperature of the fluidized polymer to avoid problems of agglomeration.

In the gas phase fluidized bed process for polymerisation of olefins the heat evolved by the exothermic polymerisation reaction is normally removed from the polymerisation zone (i.e. the fluidised bed) by means of the fluidising gas stream as described above. The hot reactor gas emerging from the top of the bed is led through one or more heat exchangers wherein the gas is cooled. The cooled reactor gas, together with any make-up gas, is then recycled to the base of the bed. In the gas phase fluidised bed polymerisation process of the present invention it is desirable to provide additional cooling of the bed (and thereby improve the space time yield of the process) by feeding a volatile liquid to the bed under conditions such that the liquid evaporates in the bed thereby absorbing additional heat of polymerisation from the bed by the "latent heat of evaporation" effect. When the hot recycle gas from the bed enters the beat exchanger, the volatile liquid can condense out. In one embodiment of the present invention the volatile liquid is separated from the recycle gas and reintroduced separately into the bed. Thus, for example, the volatile liquid can be separated and sprayed into the bed. In another embodiment of the present invention the volatile liquid is recycled to the bed with the recycle gas. Thus the volatile liquid can be condensed from the fluidising gas stream emerging from the reactor and can be recycled to the bed with recycle gas, or can be separated from the recycle gas and then returned to the bed.

The method of condensing liquid in the recycle gas stream and returning the mixture of gas and entrained liquid to the bed is described in EP-A-0089691 and EP-A-0241947. It is preferred to reintroduce the condensed liquid into the bed separate from the recycle gas using the process described in our U.S. Pat. No. 5,541,270.

A number of process options can be envisaged when using the catalysts of the present invention in an integrated process to prepare higher polymers i.e when component (d) is present. These options include "in series" processes in which the trimerisation and subsequent polymerisation are carried in separate but linked reactors and "in situ" processes in which a both reaction steps are carried out in the same reactor.

In the case of a gas phase "in situ" polymerisation process, component (d) can, for example, be introduced into the polymerisation reaction zone in liquid form, for example, as a solution in a substantially inert liquid diluent. Components (a), (b), (c) and (d) may be independently added to any part of the polymerisation reactor simultaneously or sequentially together or separately. Under these circumstances it is preferred the liquid containing the component(s) is sprayed as fine droplets into the polymerisation zone. The droplet diameter is preferably within the range 1 to 1000 microns. EP-A-0593083 discloses a process for introducing a polymerisation catalyst into a gas phase polymerization. The methods disclosed in EP-A-0593083 can be suitably employed in the polymerisation process of the present invention if desired.

Although not usually required, upon completion of polymerisation or copolymerisation, or when it is desired to terminate polymerisation or copolymerisation or at least temporarily deactivate the catalyst or catalyst component of this invention, the catalyst can be contacted with water, alcohols, acetone, or other suitable catalyst deactivators a manner known to persons of skill in the art.

The trimerisation catalyst is preferably (but optionally) added before the polymerization catalyst such that the desired primary monomer to comonomer(s) ratio is established prior to introduction of the polymerization catalyst. The desired comonomer composition at start-up may however be achieved through introduction of fresh comonomer feed or through judicious initiation of the trimerisation reaction before or during polymerization catalyst introduction.

In the presence of component (d) the polymerisation process of the present invention provides polymers and copolymers, especially ethylene polymers, at high productivity (based on the amount of polymer or copolymer produced per unit weight of complex employed in the catalyst system). This means that relatively very small quantities of transition metal complexes are consumed in commercial processes using the process of the present invention. It also means that when the polymerisation process of the present invention can be operated under polymer recovery conditions that do not employ a catalyst separation step, thus leaving the catalyst, or residues thereof, in the polymer (e.g. as occurs in most commercial slurry and gas phase polymerization processes), the amount of transition metal complex in the produced polymer can be very small.

By varying the ratio of components (a) (b), optionally (c) and (d) and/or by adding additional comonomers, catalysts of the present invention can provide a wide variety of branched polymers differing in density and in other important physical properties.

A range of polyethylene polymers are considered accessible including high density polyethylene, medium density polyethylene, low density polyethylene, ultra low density polyethylene and elastomeric materials. Particularly important are the polymers having a density in the range of 0.91 to 0.93, generally referred to in the art as linear low density polyethylene. Such polymers and copolymers are used extensively in the manufacture of flexible blown or cast film.

Poly(1-hexene), poly(1-octene) and the like are also considered accessible, as are copolymers of e.g. 1-hexene and propylene, 1-hexene and 1-octene and terpolymers of e.g. ethylene, 1-hexene and vinyl acetate.

Dienes could also be incorporated into the polymeric products to enable cross-linking for e.g. elastomer and wire and cable applications Depending upon the use of the polymer product, minor amounts of additives are typically incorporated into the polymer formulation such as acid scavengers, antioxidants, stabilizers, and the like. Generally, these additives are incorporated at levels of about 25 to 2000 ppm, typically from about 50 to about 1000 ppm, and more typically 400 to 1000 ppm, based on the polymer.

In use, polymers or copolymers made according to the invention in the form of a powder are conventionally compounded into pellets. Examples of uses for polymer compositions made according to the invention include use to form fibres, extruded films, tapes, spunbonded webs, moulded or thermoformed products, and the like. The polymers may be blown or cast into films, or may be used for making a variety of moulded or extruded articles such as pipes, and containers such as bottles or drums. Specific additive packages for each application may be selected as known in the art. Examples of supplemental additives include slip agents, anti-blocks, anti-stats, mould release agents, primary and secondary anti-oxidants, clarifiers, nucleants, uv stabilizers, and the like. Classes of additives are well known in the art and include phosphite antioxidants, hydroxylamine (such as N,N-dialkyl hydroxylamine) and amine oxide (such as dialkyl methyl amine oxide) antioxidants, hindered amine light (uv) stabilizers, phenolic stabilizers, benzofuranone stabilizers, and the like. Various olefin polymer additives are described in U.S. Pat. Nos. 4,318,845, 4,325,863, 4,590,231, 4,668,721, 4,876,300, 5,175,312, 5,276,076, 5,326,802, 5,344,860, 5,596,033, and 5,625,090.

Fillers such as silica, glass fibers, talc, and the like, nucleating agents, and colourants also may be added to the polymer compositions as known by the art.

The present invention is illustrated in the following Examples.

EXAMPLES

All manipulations were performed under anaerobic conditions. Solvents and gases were dried and degassed by standard procedures. Chemicals were purchased from the Aldrich Chemical Company unless stated otherwise. Methyl alumoxane (MAO) and modified methyl alumoxane (MMAO) were purchased from Witco as 10% w/w solutions in toluene or heptanes respectively. (2-methoxyphenyl)$_2$PN(Me)P(2-methoxyphenyl)$_2$ was synthesized by literature procedures (See example 12 of WO97/37765). Cr(p-tolyl)Cl$_2$(THF)$_3$ was synthesized by literature procedure (Daly, J. J.; Seeden, R. P. A.; J.Chem.Soc.A, 1967, 736). Reaction products were analysed by GCMS using 50 m×0.3 mm id, CP sil. CBS-MS, df=0.4 µm columns, an initial temperature of −30° C., hold 1 min, ramp rate 7° C./min, final temperature 280° C. and final hold of 5 mins. Molar quantities of catalyst are based upon the molar quantity of chromium source used in their preparation.

Example 1

A Schlenk tube was charged with CrCl$_3$(THF)$_3$ (8 mg, 0.02 mmol) and (2-methoxyphenyl)$_2$PN(Me)P(2-methoxyphenyl)$_2$ (10 mg, 0.02 mmol), 10 ml THF was added and the solution stirred for 2 hours. After this time, solvent was removed under reduced pressure and the resultant solid suspended in 50 ml toluene. MAO (4.2 ml, 6.0 mmol, 300 equivalents) was added and an immediately green solution was observed. The solution placed under an ethylene atmosphere (1 bar). An immediate exotherm was observed. The reaction was run for 60 minutes during which time the vessel was left open to a supply of ethylene at 1 bar. The catalyst was then destroyed by addition of 50 ml dilute aqueous HCl, the organic layer separated and dried over MgSO$_4$. The product mass, recorded by weighing the mass gain of the Schlenk reaction vessel, was 10.3 g.

GCMS analysis of the reaction products gave the following product distribution:

|  | wt % Total Product |
|---|---|
| Butenes | 0.04 |
| 1-Hexene | 82.17 |
| 2-Hexene | 0.44 |
| 3-Hexene | 0.15 |
| 1-Octene | 1.37 |
| Decenes | 14.39 |
| C12 olefins | 0.20 |
| C14 olefins | 0.78 |
| C16 olefins | 0.00 |
| C18 olefins | 0.00 |

Example 2

The procedure of Example 1 was followed, with the exception that 300 equivalents of MMAO (4.2 ml, 6.0 mmol) was used in place of MAO. The product mass was 8.8 g.

Example 3

The procedure of Example 1 was followed, with the exception that 100 equivalents of (iBu$_2$AlO)$_2$ (2.0M solution in toluene, 1.0 ml, 2.0 mmol) was used in place of MAO. The product mass was 1.3 g.

Example 4

The procedure as Example 1 was followed with the exception that CrCl$_2$ (3 mg, 0.02 mmol) was used in place of CrCl$_3$(THF)$_3$. The product mass was 5.6 g.

Example5

A Schlenk vessel was charged with Cr(p-tolyl)Cl$_2$(THF)$_3$ (9 mg, 0.02 mmol) and (2-methoxyphenyl)$_2$PN(Me)P(2-methoxyphenyl)$_2$ (10 mg, 0.02 mmol), 50 ml toluene was added, and the solution stirred for 5 minutes. MMAO (4.2 ml, 6.0 mmol) 300 equivalents) was added and the solution placed under an ethylene atmosphere (1 bar). The reaction was run for 60 minutes during which time the vessel was left open to a supply of ethylene at 1 bar. The reaction was worked-up as described in example 1. The product mass was 11.0 g.

Example 6

The procedure as Example 1 was followed with the exception that 0.04 mmol (20 mg) of (2-methoxyphenyl)$_2$PN(Me)P(2-methoxyphenyl)$_2$ was used rather than 0.02 mmol. The product mass was 9.5 g.

Example 7

The procedure as Example 2 was followed with the exception that 0.01 mmol (5 mg) of (2-methoxyphenyl)$_2$PN(Me)P(2-methoxyphenyl)$_2$ was used rather than 0.02 mmol. The product mass was 3.3 g.

Example 8

A Schlenk tube was charged with (2-methoxyphenyl)$_2$PN(Me)P(2-methoxyphenyl)$_2$ (415 mg, 0.8 mmol) and CrCl$_3$(THF)$_3$ (300 mg, 0.8 mmol) and 30 ml dichloromethane added. A bright blue solution formed almost immediately which was stirred for 2 hours. After this time solvent was removed under reduced pressure to yield a blue solid; this was washed with diethyl ether and dried in vacuo. A further Schlenk tube was charged with mg of this compound and 50 ml toluene added. MMAO (16.8 ml, 24 mmol, 300 equivalents) was added and the solution placed under an ethylene atmosphere (1 bar). The reaction was run for 60 minutes during which time the vessel was left open to a supply of ethylene at 1 bar. The reaction was worked-up as described in example 1. The product mass was 2.5 g.

Example 9

Preparation of MAO on Silica

Toluene (200 ml) was added to a vessel containing silica (prepared according to procedures described in WO 99/12981 example 37.1. Silica was supplied by Crosfield as grade ES70X, calcined at 200° C. overnight, 20.5 g after calcination) under an inert atmosphere. The slurry was mechanically stirred and MAO (1.5 M, 62.1 mmol, 41.4 ml) was added via syringe. The mixture was stirred for 1 hour at 80° C. before removing excess toluene and drying under vacuum to obtain 15% w/w MAO on silica in quantitative yield.

Trimerisation Using a Supported Catalyst Composition

A Schlenk vessel was charged with CrCl$_3$(THF)$_3$ (8 mg, 0.02 mmol) and (2-methoxyphenyl)$_2$PN(Me)P(2-methoxyphenyl)$_2$ (10 mg, 0.02 mmol), 10 ml THF was added and the solution stirred for 2 hours. After this time, solvent was removed under reduced pressure and the resultant solid suspended in 20 ml toluene. MAO (1.4 ml, 2 mmol, 100 equivalents) was added and an immediately a green solution was observed. This solution was then transferred via cannula to a Schlenk tube containing a slurry of 15% w/w MAO on silica (prepared as described above) in toluene (1 g of MAO/Silica in 30 ml toluene). The green colour of the solution was quickly transferred onto the silica/MAO and a colourless supernatant remained. This slurry was stirred and placed under an ethylene atmosphere (1 bar). The reaction was run for 60 minutes during which time the vessel was left open to a supply of ethylene at 1 bar. The reaction was worked-up as described in example 1. The product mass was 8.9 g.

|  | wt % Total Product |
|---|---|
| 1-Hexene | 62 |
| Octenes | 0.28 |
| Decenes | 30.3 |

Example 10

A Schlenk vessel was charged with CrCl$_3$(THF)$_3$ (8 mg, 0.02 mmol) and (2-methoxyphenyl)$_2$PN(Me)P(2-methoxyphenyl)$_2$ (10 mg, 0.02 mmol), 10 ml THF was added and the solution stirred for 2 hours. After this time, solvent was removed under reduced pressure, the resultant solid suspended in 10 ml toluene and MAO (4.2 ml, 6.0 mmol, 300 equivalents) added. This solution was then injected into an autoclave at 8 bar ethylene pressure and 50° C. The diluent was isobutane. The reaction was run for 1 hour at 8 bar ethylene pressure and 50° C. after which time ethylene and isobutane gases were vented. The reaction products were then worked up as described in Example 1. The mass of product recovered was 40.0 g and the productivity over one hour was 2000 g/mmol.h. GCMS analysis gave the following product distribution:

|  | wt % Total Product |
|---|---|
| Butenes | 0.00 |
| 1-Hexene | 88.37 |
| 2-Hexene | 0.12 |
| 3-Hexene | 0.00 |
| Octenes | 3.95 |
| Decenes | 6.61 |
| C12 olefins | 0.33 |
| C14 olefins | 0.20 |
| C16 olefins | 0.00 |
| C18 olefins | 0.00 |

Example 11

The procedure of Example 10 was followed with the following exceptions: 500 ml toluene diluent was used in place of isobutene and 0.01 mmol of catalyst was used. The reactor conditions were maintained at 50° C. and 8 bar ethylene pressure over the 60 minute run time. A stable gas uptake profile over the run time was observed. The mass of product recovered was 72.7 g and the productivity over one hour was 7270 g/mmol.h (134 700 g/gCr.h.)

|  | wt % Total Product |
|---|---|
| 1-Hexene | 86 |
| Octenes | 1.8 |
| Decenes | 8.7 |

Example 12

The procedure of Example 11 was followed with the exceptions that the reactor conditions were maintained at 80° C. and 20 bar ethylene pressure over the 60 minute run time. 0.0025 mmol of catalyst was used. The mass of product recovered was 141 g and the productivity over one hour was 56400 g/mmol.h (1 033 200 g/gCr.h.)

|  | wt % Total Product |
|---|---|
| 1-Hexene | 88.8 |
| Octenes | 1.8 |
| Decenes | 7.4 |

Example 13

The procedure of Example 11 was followed with the exceptions that the reactor conditions were maintained at 108° C. and 8 bar ethylene pressure over the 60 minute run time. 0.01 mmol of catalyst was used. The mass of product recovered was 51.6 g and the productivity over one hour was 5160 g/mmol.h (95 900 g/gCr.h)

|  | wt % Total Product |
|---|---|
| 1-Hexene | 86.6 |
| Decenes | 11 |

Example 14

The procedure of Example 11 was followed with the exceptions that 1 bar of hydrogen was added to the reactor before the run. 0.01 mmol of catalyst was used. The mass of product recovered was 94.7 g and the productivity over one hour was 9470 g/mmol.h (175 300 g/gCr.h.)

|  | wt % Total Product |
|---|---|
| 1-Hexene | 82 |
| Octenes | 0.45 |
| Decenes | 13.2 |

Example 15

The procedure of Example 11 was followed with the exception that 0.01 mmol of a supported catalyst, prepared as described in Example 8, was used. The mass of product recovered was 49.8 g and the productivity over one hour was 4980 g/mmol.h (90 406 g/gCr.h.)

|  | wt % Total Product |
|---|---|
| 1-Hexene | 89 |
| Octenes | 0.58 |
| Decenes | 7.9 |

Example 16

The procedure of Example 11 was followed with the exceptions that 100 ml of 1-butene was added to the reactor before the run and 400 ml of toluene diluent was used. The reactor conditions were maintained at 80° C. and 4 bar ethylene pressure. 0.02 mmol of catalyst was used. The mass of product recovered was 49.4 g and the productivity over one hour was 2470 g/mmol.h (46125 g/gCr.h.)

|  | wt % Total Product |
|---|---|
| 1-Hexene | 60 |
| Octenes | 25 |
| Decenes | 10.9 |

Example 17

The procedure of Example 1 was followed with the exceptions that the run time in this case was 90 minutes and the product mass was recorded by weighing the mass gain of the Schlenk reaction vessel at various times through the run.

|  | Time (mins) | | | | |
|---|---|---|---|---|---|
|  | 15 | 30 | 45 | 60 | 90 |
| Mass gain (g) | 2.7 | 5.2 | 7.6 | 10.0 | 13.0 |

GCMS analysis of the product after 90 minutes gave the following product distribution:

|  | wt % Total Product |
|---|---|
| Butenes | 0.00 |
| 1-Hexene | 64.10 |
| 2-Hexene | 0.13 |
| 3-Hexene | 0.00 |
| Octenes | 0.44 |
| Decenes | 28.93 |
| C12 olefins | 0.13 |
| C14 olefins | 4.99 |
| C16 olefins | 0.00 |
| C18 olefins | 0.59 |

Example 18

The procedure of Example 2 was followed with the exceptions that 20 ml of toluene was used and 20 ml of 1-dodecene was added at the start of the run. The product mass was 2.1 g.

|  | wt % Total Product |
|---|---|
| 1-Hexene | 37 |
| Decene | 27 |
| C16 olefins | 29 |

Example 19

The procedure of Example 2 was followed with the exceptions that 20 ml of toluene was used and 20 ml of 1-tetradecene was added at the start of the run. The product mass was 3.2 g.

|  | wt % Total Product |
|---|---|
| 1-Hexene | 35.3 |
| Decene | 6.7 |
| C18 olefins | 50.8 |

Example 20

The procedure of Example 9 was followed with the exceptions that 20 ml of toluene was used and 20 ml of 1-dodecene was added at the start of the run, in this case the run was for 4.5 hours. The product mass was 7.5 g.

| | wt % Total Product |
|---|---|
| 1-Hexene | 38 |
| Decene | 24 |
| C16 olefins | 38 |

Example A (Comparative)

The procedure of Example 1 was followed with the exceptions that 1,2-bis(diphenylphosphino)ethane (8 mg, 0.02 mmol) was used in place of (2-methoxyphenyl)$_2$PN(Me)P(2-methoxyphenyl)$_2$. No product was formed.

Example 21

The procedure of Example 1 was followed, with the exception that tris(2-methoxymethoxyphenyl)phosphane (18 mg, 0.04 mmol) was used in place of (2-methoxyphenyl)$_2$PN(Me)P(2-methoxyphenyl)$_2$. The product mass was 1.2 g.

GCMS analysis of the reaction products gave the following product distribution:

| | wt % Total Product |
|---|---|
| 1-Hexene | 90.66 |
| 2-Hexene | 2.94 |
| 1-Octene | 2.85 |
| Decenes | 3.54 |

Example B (Comparative)

The procedure of Example 20 was followed with the exception that triphenylphosphane (11 mg, 0.04 mmol) was used in place of tris(2-methoxymethoxyphenyl)phosphane. No product was formed

Example 22

(Co)Polymerisation of Ethylene

An autoclave was charged with isobutane (500 ml) and triethylaluminium (2.0M solution in toluene, 1.5 ml, 3 mmol). The autoclave was pressurized to 8 bar ethylene pressure and heated to 50° C.

A catalyst (0.02 mmol), prepared as described in Example 8, was then injected as a slurry in 10 ml toluene. Almost immediately, a slurry of Ziegler catalyst (0.05 g), prepared according to U.S. Pat. No. 5,470,812, example A, was injected as a slurry in 10 ml toluene. The reaction was run for 1 hour at 8 bar ethylene pressure and 50° C. after which time ethylene and isobutane gases were vented. The resultant polymer was washed with dilute aqueous HCl and then methanol and dried in vacuo. The mass of polymer recovered was 36.0 g. NMR spectroscopy of the polymer shows the presence of butyl branches, indicating that an ethylene/1-hexene copolymer was produced.

Example 23

(Co)Polymerisation of Ethylene

A supported catalyst (0.01 mmol) was prepared as described in Example 9 in 40 ml toluene. In a separate Schlenk tube, [rac-(ethylene bridged bis indenyl) zirconium dichloride] (mg, 0.01 mmol) was disolved in 10 ml toluene and MMAO (7 ml, 10.0 mmol, 1000 equivalents) added. This second solution was added via canula to the supported catalyst slurry and the resultant slurry stirred under an ethylene atmosphere at 1 bar. The reaction was run for 60 minutes during which time the vessel was left open to a supply of ethylene at 1 bar. The catalysts were then destroyed by careful addition of 50 ml dilute aqueous HCl. Both organic and aqueous fractions were then added to 500 ml of acetone, causing precipitation of the polymer produced. The polymer was washed with further portions of acetone and dried in vacuo. The mass of polymer recovered was 3.4 g. NMR spectroscopy of the polymer shows the presence of butyl branches, indicating that an ethylene/1-hexene copolymer was produced.

The invention claimed is:

1. A process for the trimerization of olefins, comprising contacting a monomeric olefin or mixture of olefins under trimerization reaction conditions in a trimerization reactor with a catalyst to produce a trimerization reaction product, which catalyst comprises:

(a) a source of a Group 3 to 10 transition metal:

(b) a ligand selected from the group consisting of:
(2-methoxyphenyl)(phenyl)PN(Me)P(phenyl)$_2$,
(2-methoxyphenyl)$_2$PN(Me)P(phenyl)$_2$,
(2-methoxyphenyl)(phenyl)PN(Me)P(2-methoxyphenyl)(phenyl),
(2-methoxyphenyl)$_2$PN(Me)P(2-methoxyphenyl)$_2$,
(2-ethoxyphenyl)$_2$PN(Me)P(2-ethoxyphenyl)$_2$,
(2-isopropoxphenyl)$_2$PN(Me)P(2-isopropoxyphenyl)$_2$,
(2-hydroxyphenyl)$_2$PN(Me)P(2-hydroxyphenyl)$_2$,
(2-nitrophenyl)$_2$PN(Me)P(2-nitrophenyl)$_2$,
(2,3-dimethoxyphenyl)$_2$PN(Me)P(2,3-dimethoxyphenyl)$_2$,
(2,4-dimethoxyphenyl)$_2$PN(Me)P(2,4-dimethoxyphenyl)$_2$,
(2,6-dimethoxyphenyl)$_2$PN(Me)P(2,6-dimethoxyphenyl)$_2$,
(2,4,6-trimethoxyphenyl)$_2$PN(Me)P(2,4,6-trimethoxyphenyl)$_2$,
(2-dimethoxyphenyl)(2-methylphenyl)PN(Me)P(2-methylphenyl)$_2$,
[2-(dimethylamino)phenyl]$_2$PN(Me)P[2-(dimethylamino)phenyl]$_2$,
(2-methoxymethoxyphenyl)$_2$PN(Me)P(2-methoxymethoxyphenyl)$_2$,
(2-methoxyphenyl)$_2$PN(Ethyl)P(2-methoxyphenyl)$_2$,
(2-methoxyphenyl)$_2$PN(Phenyl)P(2-methoxyphenyl)$_2$,
(2-methoxyphenyl)$_2$PN(Me)N(Me)P(2-methoxyphenyl)$_2$,
(2-methoxyphenyl)$_2$PCH$_2$P(2-methoxyphenyl)$_2$(2-methoxyphenyl)$_2$PCH$_2$CH$_2$P(2-methoxyphenyl)$_2$,

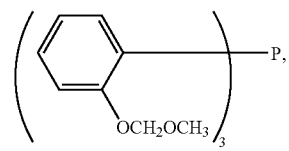

tri(2-methoxymethoxyphenyl)phosphane; and optionally (c) an activator.

2. The process according to claim 1, wherein the catalyst is supported.

3. The process according to claim 2, wherein the support is selected from the group consisting of silica, alumina, $MgCl_2$, zirconia, polyethylene, polypropylene, polystyrene, and poly(aminostyrene).

4. The process according to claim 1, wherein component (a) is a source of chromium, molybdenum or tungsten.

5. The process according to claim 1, wherein component (c) is selected from the group consisting of trimethylaluminium (TMA), triethylaluminium (TEA), tri-isobutylaluminium (TIBA), tri-n-octylaluminium, methylaluminium dichloride, ethylaluminium dichloride, dimethylaluminium chloride, diethylaluminium chloride, ethylaluminiumsesquichloride, methylaluminiumsesquichloride, alumoxanes, tetrafluoroboric acid etherate, silver tetrafluoroborate, sodium hexafluoroantimonate, boroxines, $NaBH_4$, trimethylboron, triethylboron, dimethylphenylammonium-tetra(phenyl)borate, trityltetra(phenyl)borate, triphenylboron, dimethylphenylammonium tetra(pentrafluorophenyl)borate, sodium tetrakis[(bis-3,5-trifluoromethyl)phenyl]borate, $H^+(OEt_2)_2$[(bis-3,5-trifluoromethyl)phenyl]borate, trityltetra(pentrafluorophenyl)borate and tris(pentafluorophenyl)boron, and mixtures thereof.

6. The process according to claim 1, wherein the olefin or mixture of olefins is additionally contacted with a further catalyst (d) suitable for the polymerization, oligomerization or other chemical transformation of olefins, such that the trimerization product is incorporated into a higher polymer or other chemical product.

7. The process according to claim 1, wherein the monomeric olefin is ethylene.

8. The process of claim 1, wherein the mixture of olefins comprises ethylene and one or more $C_3$–$C_{36}$ monoolefin.

9. The process according to claim 8, wherein the $C_3$–$C_{36}$ monoolefin is a $C_4$–$C_{20}$ monoolefin.

10. The process according to claim 9, wherein the $C_4$–$C_{20}$ monoolefin is butene, hexene, decene, a $C_{12}$ olefin or a $C_{14}$ olefin.

11. The process according to claim 1, wherein at least 85 wt % of the trimerization reaction product is one of the following: 1-hexene, 1-octene, 1-decene, a $C_{12}$olefin, a $C_{14}$olefin, a $C_{16}$olefin, or a $C_{18}$olefin.

12. The process according to claim 1, wherein the reaction temperature is less than 100° C., and/or the reaction pressure is below 30 bara.

13. The process according to claim 1, wherein the residence time in the trimerization reactor is less than 4 hours.

14. The process according to claim 1, wherein the trimerization reaction conditions are solution phase, slurry phase or gas phase.

15. The process according to claim 14, wherein the reaction is conducted under gas phase fluidized bed conditions.

16. The process according to claim 6, wherein the trimerization reactor is upstream or downstream of at least one polymerization or oligomerization reactor.

17. The process according to claim 6, wherein the trimerization reactor is incorporated into a reaction loop of at least one polymerization or oligomerization reactor.

18. The process according to claim 17, wherein the trimerization reactor is incorporated into a side-stream taken from said reaction loop.

19. The process according to claim 6, wherein the trimerization reaction product is produced in or introduced into at least one polymerization or oligomerization reactor.

20. The process according to claim 6, wherein at least one trimerization reaction product is separated from a remainder of the trimerization reaction products prior to (re)introduction into the polymerization or oligomerization reactor.

21. The process according to claim 1, wherein the trimerization reaction is conducted in the presence of hydrogen and/or a halide source.

* * * * *

UNITED STATES PATENT AND TRADEMARK OFFICE
CERTIFICATE OF CORRECTION

PATENT NO. : 7,141,633 B2
APPLICATION NO. : 10/920262
DATED : November 28, 2006
INVENTOR(S) : Duncan Frank Wass It is certified that error appears in the above-identified patent and that said Letters Patent is hereby corrected as shown below:

Claim 1, Column 22, Line 63, insert --, and-- after the formula.

Claim 1, Column 22, Line 64, "tri(2-methoxymethoxyphenyl)phosphane" should read --tri(2-methoxyphenyl)phosphane--.

Signed and Sealed this

Second Day of December, 2008

JON W. DUDAS
*Director of the United States Patent and Trademark Office*